United States Patent [19]

Hart

[11] 4,386,928

[45] Jun. 7, 1983

[54] FEMININE HYGIENIC DEVICE

[76] Inventor: Nathan C. Hart, Rte. 2, Box 1049, Odessa, Fla. 33556

[21] Appl. No.: 255,657

[22] Filed: Apr. 20, 1981

[51] Int. Cl.³ .............................................. A61M 3/00
[52] U.S. Cl. ......................................................... 604/83
[58] Field of Search ................. 128/229, 66, 224, 251; 604/82, 83, 84, 85, 118, 150

[56] References Cited

U.S. PATENT DOCUMENTS

| | | | |
|---|---|---|---|
| 2,272,381 | 2/1942 | Marvin | 128/229 |
| 2,957,476 | 10/1960 | Freeman | 128/229 |
| 3,104,664 | 9/1963 | Ladd | 128/229 |
| 3,373,744 | 3/1968 | Kendall | 128/229 |
| 3,533,409 | 10/1970 | Greer | 128/229 |

Primary Examiner—John D. Yasko
Attorney, Agent, or Firm—Arthur W. Fisher, III

[57] ABSTRACT

A feminine hygienic device for use with a pressurized water supply, the feminine hygienic device comprising a housing configured to be coupled to the pressurized water supply wherein the housing includes a mixing chamber having a fluid reservoir formed therein, an inlet port having a one-way control valve disposed therein to contain fluid medication in the mixing chamber and to selectively control the flow of water from the pressurized water supply to the mixing chamber, a first outlet port having a quick disconnect coupling device disposed adjacent thereto and a second outlet port having a diverter control valve having at least two positions disposed in operative communication therewith to selectively control the flow of liquid from the mixing chamber through the first and second outlet ports in combination with a dispensing nozzle including a flow control and metering control coupled to the first outlet port to selectively control the flow of liquid from the mixing chamber through the dispensing nozzle for use by the operator.

10 Claims, 3 Drawing Figures

U.S. Patent  Jun. 7, 1983  4,386,928
FIG. 1
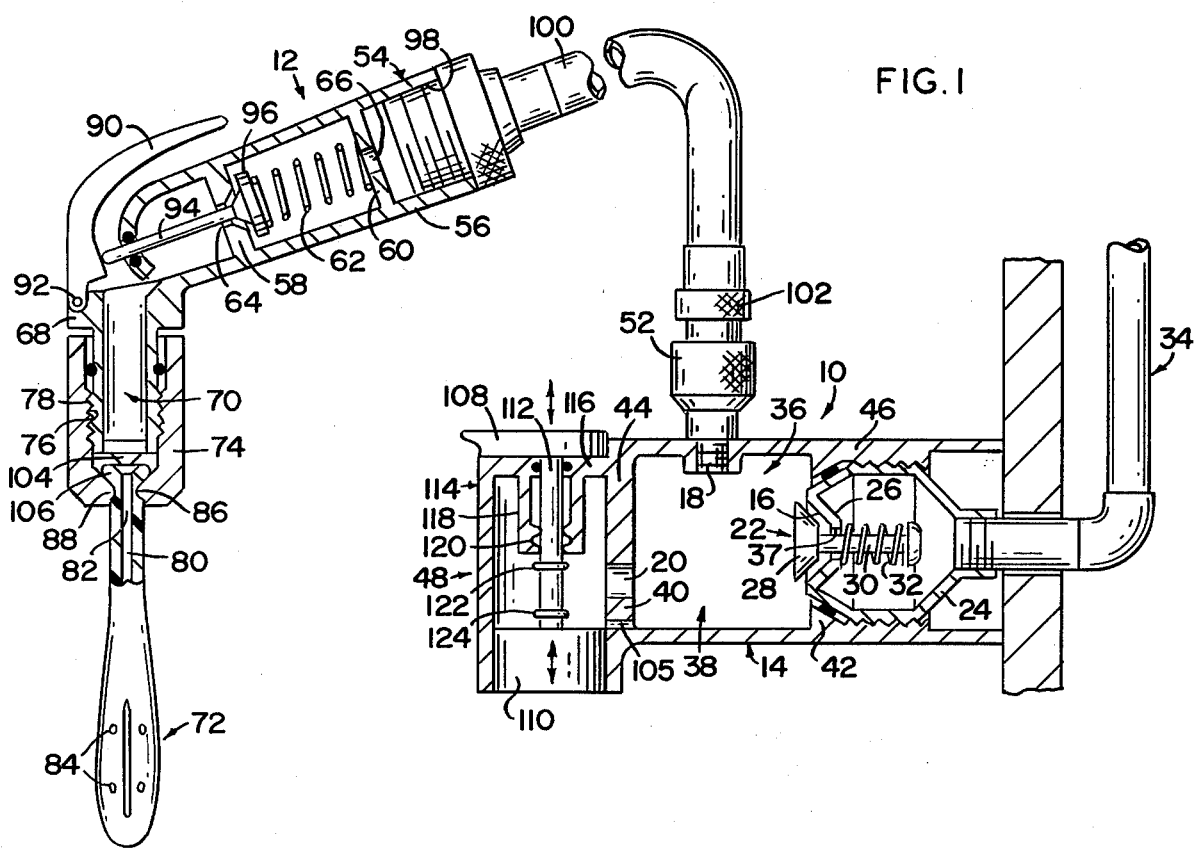
FIG. 2
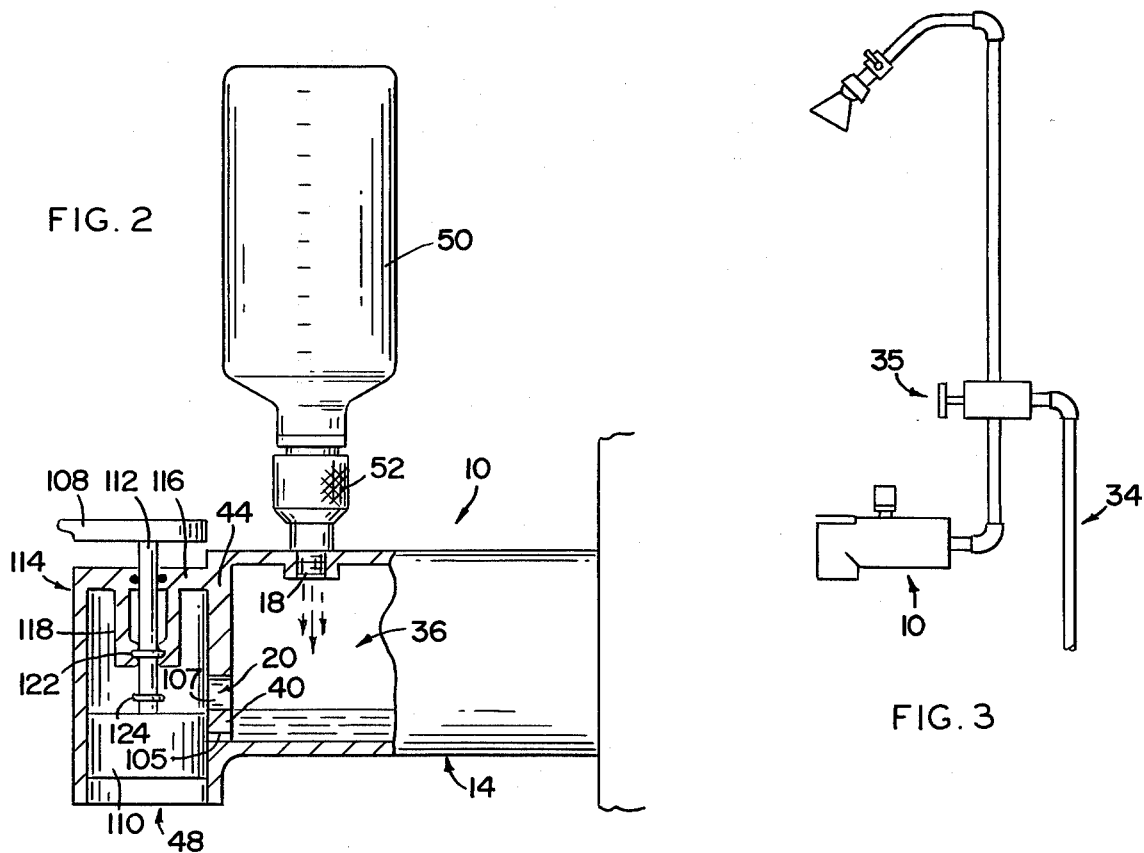
FIG. 3

FEMININE HYGIENIC DEVICE

BACKGROUND OF THE INVENTION

1. Field of the Invention

A feminine hygienic device including a mixing chamber and dispensing nozzle for use with a pressurized water supply.

2. Description of the Prior Art

Typically, hospitals and similar institutions have permanently mounted irrigation type hygienic devices. These devices are complicated, expensive and generally unsightly. Thus, these permanently mounted irrigation devices are rarely used in the private home. Permanent mount-type has sufficient pressure but not controlled properly for safe and convenient use. More commonly, the bag-type douche or irrigation device utilizing gravity to compel the water to flow therethrough are used. In this type device the discharge of the mixture of water and medication is not at a sufficiently high pressure to effect a proper cleansing action.

Moreover, utilization of vaginal syringes has been curtailed, different people require different fluid or water pressures due to their age, health and delicate wall tissue condition. In addition, and perhaps of maximum importance, the applicator or syringe must be readily adaptable to being cleansed with a minimum of effort and should be capable of being attached and detached from the pressure source with ease.

Numerous devices for this general purpose have been proposed in the past, but have fallen short of the accomplishment of the desired ends in various aspects. Many have been designed to become a temporary attachment to a water faucet and do not permit its full utilization since the attached apparatus necessarily interferes with the normal operation and action of the faucet. Additionally some have been designed to be permanently installed at great expense and are insufficiently controlled to provide safe and convenient use.

Examples of such prior art are found in U.S. Pat. Nos. 1,752,782; 2,664,892; 2,272,381; 2,278,055; 3,104,664; 3,373,744; 3,669,101; 3,682,176; and 4,000,742.

SUMMARY OF THE INVENTION

The present invention relates to a feminine hygienic device for use with a pressurized water supply.

The housing comprises a body member having an inlet port together with a first and second outlet port. A diverter control valve is located at the second outlet port and a one-way control valve is disposed within the housing to selectively control the flow of water from the pressurized water system to the mixing chamber. The valve member normally closes the inlet port to insure containment of the fluid medication in mixing chamber reservoir.

The housing further includes a fluid reservoir formed in the lower portion thereof which permits the measuring of a fluid medication in the mixing chamber up to the level of the second outlet port A resilient supply container may be coupled to the housing and mixing chamber to permit feeding fluid medication through the first outlet port into the mixing chamber and fluid reservoir.

The dispensing nozzle comprises a body member having a lower hollow housing and a nozzle coupler having a passage formed centrally therein. A quick disconnect syringe is operatively held in communication with the passage by means of an attachment member. Attachment member and nozzle coupler include internal and external threads to permit lateral movement therebetween. This in combination with the inner portion of the quick disconnect syringe form a metering control as more fully described hereinafter. A fluid channel is formed along the longitudinal axis of the quick disconnect syring permitting fluid communication from the interior portion thereof and the outer portion including a plurality of apertures. The dispensing nozzle further includes a flow control comprising a handle pivotally coupled to the nozzle coupler which is disposed to operatively engage a stem to selectively open and close a aperture as more fully described hereinafter. The lower portion of stem comprises an enlarged seat portion which normally seats. The dispensing nozzle further includes internally threaded portion to engage the one end of a hose which in turn is coupled to the quick disconnect coupling means at the opposite end thereof.

In operation, the conventional mixture control valve is closed removing any pressure in the pressurized water supply acting against the one way control valve. With the diverter control valve in the open position and the resilient supply container operatively coupled to the quick disconnect couple, fluid medication is supplied to the mixing chamber to the level of the fluid reservoir. Any excess will flow from the second outlet port. Once filled the diverter control valve is closed and the dispensing nozzle is operatively coupled to the quick disconnect coupling means. With the conventional mixture control valve in the open position pressure is exerted against the one way control valve causing it to unseat and permitting water to flow into the mixing chamber. With the flow control handle depressed liquid is free to flow from the mixing chamber through apertures through channel and through the quick disconnect syringe. The rate of flow may be adjusted by moving the attachment longitudinally relative to the nozzle coupler such that the metering control including a first metering element comprising a metering pin formed on the forward portion of the nozzle coupler and a second metering element comprising an nnular flange formed on the inner portion of the syringe determines the effective diameter of the inner portion of channel. Once the proper rate is metered by such adjustable the assembly is ready for use.

The invention accordingly comprises the features of construction, combination of elements, and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which:

FIG. 1 is a cross sectional side view of the feminine hygienic device.

FIG. 2 is a partial cross sectional view of the feminine hygienic device.

FIG. 3 is a side view of the feminine hygienic device with pressurized water supply.

Similar reference characters refer to similar parts throughout the several views of the drawings.

DETAILED DESCRIPTION OF THE PREFERRED EMBODIMENT

As shown in FIGS. 1 through 3, the present invention relates to a feminine hygienic device for use with a pressurized water supply. As best shown in FIG. 1, the feminine hygienic device comprises a housing and dispensing nozzle generally indicated as 10 and 12 respectively.

The housing 10 comprised a body member 14 having an inlet port together with a first and second outlet port generally indicated as 16, 18, and 20 respectively formed therein. A one-way control valve 22 comprising a valve body, valve flange, valve member, valve stem and bias means indicated as 24, 26, 28, 30 and 32 respectively is disposed within the housing 10 to selectively control the flow of water from the pressurized water system 34 and to contain fluid medication in the mixing chamber 36. The pressurized water system 34 includes a conventional mixture control valve 35 as best shown in FIG. 3. The valve member 28 normally closes the inlet port 16 under the influence of the bias means 32 when the conventional mixture control valve 35 is closed by valve member 28 seating on valve flange 26 closing aperture 37 formed in valve flange 26.

The housing 10 further includes a fluid reservoir 38 formed in the lower portion thereof formed by the lower portions 49 and 42 of end walls 44 and 46 respectively. As best shown in FIG. 2, this permits the addition of fluid medication to the mixing chamber 36 up to the level of the fluid reservoir 38 which is limited or defined by the height of the lower portion 40 of end wall 44. This is accomplished while the conventional mixture control valve 35 is closed and the diverter control valve 48 is in the open position which permits flow of excess fluid medication from the second outlet port 20. As shown in FIG. 2, a resilient supply container 50 may be coupled to the housing 10 and mixing chamber 36 by a quick disconnect coupling 52 to permit feeding of fluid medication through the first outlet port 18 into the mixing chamber 36 and fluid reservoir 38.

The quick disconnect coupling 52 may comprise any suitable means to cooperatively mate with the resilient supply container 50 and the dispensing nozzle 12 as more fully described hereinafter.

As best shown in FIG. 1, the dispensing nozzle 12 comprises a body member 54 having a lower hollow housing 56 including first and second retainer means 58 and 60 respectively to operatively receive a bias means 62 therein. The first and second retainer means 58 and 60 further include apertures 64 and 66 respectively to permit flow of liquid as more fully described hereinafter. Extending outwardly from the upper portion of the lower housing 56 is a nozzle coupler 68 having a passage 70 formed centrally therein. A quick disconnect syringe generally indicated as 72 is operatively held in communication with passage 70 by means of an attachment member 74. Attachment member 74 and nozzle coupler 68 include internal and external threads 76 and 78 respectively to permit lateral movement therebetween. This in combination with the inner portion of the quick disconnect syringe 72 form a metering control as more fully described hereinafter. A fluid channel 80 is formed along the longitudinal axis of the quick disconnect syringe 72 permitting fluid communication from the interior portion generally indicated as 82 thereof and the outer portion including a plurality of apertures each indicated as 84. The quick disconnect syringe 72 includes an annular retainer groove 86 formed on the end portion thereof to cooperatively engage the annular ridge 88 formed on the end portion of attachment member 74. Alternately, a quick disconnect two position bidet head may be interchanged with the syringe. The dispensing nozzle 12 further includes a flow control comprising a handle 90 pivotally coupled to the nozzle coupler 68 by pin or hinge 92 which is disposed to operatively engage a stem 94 to selectively open and close aperture 64 as more fully described hereinafter. The lower portion of stem 94 comprises an enlarged seat portion 96 which normally seats against first retainer means 58 under the influence of the bias 62. The stem 94 and enlarged seat portion 96 cooperatively for a valve. The dispensing nozzle 12 further includes internally threaded portion 98 to engage the one end of hose 100 which in turn is coupled to the quick disconnect coupling means 102 at the opposite end thereof.

FIG. 2 shows an alternate housing 10 and diverter control valve 48. The forward end wall 44 includes a second or upper outlet port 107 and third or lower outlet port 105. The diverter control valve 48 comprises a control handle 108 interconnected to a valve member 110 by an interconnecting stem 112. The diverter control valve 48 is operatively supported by the forward portion of the housing 10 comprising a diverter valve housing 114 including support shelf 116 having a retainer member 118 extending downwardly from the central portion thereof. A retainer element comprising a retainer groove 120 is formed on the lower portion thereof. A first and second detent or ridge 122 and 124 are formed on the outer surface of the interconnecting stem 112.

In operation, the conventional mixture control valve 35 is closed removing any pressure in the pressurized water supply 34 acting against the one way control valve 22. With the diverter control valve 48 in the open position and the resilient supply container 50 operatively coupled to the quick disconnect couple 52, fluid medication is supplied to the mixing chamber 36 to the level of the fluid reservoir 38. Any excess will flow from the second outlet port 20. Once filled the diverter control valve 48 is closed and the dispensing nozzle 12 is operatively coupled to the quick disconnect coupling means 52. With the conventional mixture control valve 35 in the open position pressure is exerted against the one way control valve 22 causing it to unseat and permitting water to flow into the mixing chamber 42. With the flow control handle 90 depressed liquid is free to flow from the mixing chamber 36 through apertures 54 and 66 through channel 70 and through the quick disconnect syringe 72. The rate of flow may be adjusted by moving the attachment 74 longitudinally relative to the nozzle coupler 68 such that the metering control including a first metering element comprising a metering pin 104 formed on the outer of the nozzle coupler 68 and a second metering element comprising an annular flange 106 formed on the inner portion of the syringe 72 determines the effective diameter of the inner portion of channel 82. Once the proper rate is metered by such adjustable the assembly is ready for use.

The three position diverter control valve 48 is movable between a lower, intermediate and upper position. In the lower position with the control handle 108 resting on the support shelf 116 the valve member 110 closes neither the second or third outlet ports 107 and 105 fluid is free to drain from the reservoir 38 through the third outlet port 105. The diverter control valve 48 is held in the intermediate position by the operative engagement of the first detent 122 with the retainer groove 120 to close the third outlet port 105 permitting the operator to fill the fluid reservoir 38 as previously described. The diverter control valve 48 is held in the upper position by the operative engagement of the second detent 124 with the retainer groove 120 to close both the second and third outlet ports 107 and 105 to ensure flow of the pressured fluid medication as previously described. When pressure is applied with the control valve 48 in the lower position water will follow therefrom for normal use.

It will thus be seen that the objects set forth above, and those made apparent from the preceding description are efficiently attained and since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which as a matter language, might be said to fall therebetween.

Now that the invention has been described,

What is claimed is:

1. A feminine hygienic device for use with a pressurized water supply, said feminine hygienic device comprising a housing configured to be coupled to the pressurized water supply wherein said housing includes a body member including a pair of end walls formed on opposite ends thereof, a mixing chamber formed in said body member having a fluid reservoir formed in the lower portion thereof, to receive a predetermined volume of fluid medication therein, an inlet port disposed within said body member on one of said end walls having a one-way control valve disposed therein to selectively control the flow of water from the pressurized water supply to said mixing chamber, a first outlet portion formed on the upper portion of said body member having a coupling device disposed adjacent thereto and a second outlet port formed on said end wall opposite said inlet port having a diverter control valve including a valve member movable between a lower and upper position disposed in operative communication therewith to selectively control the flow of liquid from said mixing chamber through said first outlet port when in said upper position and through said second outlet port when in said lower position.

2. The feminine hygienic device of claim 1 wherein said second outlet port is formed in the mid-portion of said end wall to control the predetermined volume of fluid medication retained within said fluid reservoir.

3. The feminine hygienic device of claim 2 wherein said body member further includes a third outlet port formed in the lower portion thereof and said diverter control valve is movable between a lower, intermediate and upper position such that the fluid may drain from said fluid reservoir when said diverter control valve is in said lower position through said third outlet port, said diverter control valve closing said third outlet port when said diverter control valve is in said intermediate position such that said fluid reservoir may receive a predetermined volume of fluid medication therein, and liquid flows from said mixing chamber through said first outlet port when said diverter control valve is in said upper position.

4. The feminine hygienic device of claim 1 further including a dispensing nozzle including a flow control and metering control coupled to said first outlet port to selectively control the flow of liquid from said mixing chamber through said dispensing nozzle for use by the operator.

5. The feminine hygienic device of claim 4 wherein said dispensing nozzle comprises a body member having a lower hollow housing and an upper nozzle coupler including a passage formed centrally therein, and a syringe operatively coupled to said nozzle coupler by an attachment member movably coupled to said nozzle coupler.

6. The feminine hygienic device of claim 5 wherein a first and second retainer means each including apertures formed therein is disposed within said lower housing in combination with a handle movable between an open and closed position and valve member, said valve member being disposed to selectively close said aperture of said first retainer means to cooperatively form said flow control.

7. The hygienic device of claim 5 further including a first metering element formed on the outer portion of said nozzle coupler and a second metering element formed on the inner portion of syringe movable relative to each other to cooperatively form said meter control.

8. The hygienic device of claim 7 wherein said first metering element comprises a metering pin, said second metering element comprising an annular flange, said metering pin disposed to extend into said annular flange.

9. The hygienic device of claim 8 wherein said syringe further includes an annular retainer groove formed on the inner portion thereof and said attachment member including an annular ridge formed on the outer portion thereof to cooperatively attach said nozzle to said attachment member.

10. The feminine hygienic device of claim 1 wherein said diverter control valve further includes a retainer member having a retainer element and a first and second detent disposed to selectively engage said retainer element to secure said diverter control valve in said intermediate position to close said second outlet port and in said upper position to close said second and third outlet ports.

* * * * *